(12) United States Patent
Hayes et al.

(10) Patent No.: US 11,382,671 B2
(45) Date of Patent: Jul. 12, 2022

(54) SURGICAL INSTRUMENT AND METHOD

(71) Applicant: Warsaw Orthopedic, Inc, Warsaw, IN (US)

(72) Inventors: Robert Chastain Hayes, Nashville, TN (US); Brian A. O'Shaughnessy, Nashville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 175 days.

(21) Appl. No.: 16/452,127

(22) Filed: Jun. 25, 2019

(65) Prior Publication Data

US 2020/0405359 A1 Dec. 31, 2020

(51) Int. Cl.
*A61B 17/70* (2006.01)
*A61B 17/00* (2006.01)

(52) U.S. Cl.
CPC ...... *A61B 17/7079* (2013.01); *A61B 17/7001* (2013.01); *A61B 2017/0042* (2013.01); *A61B 2017/00407* (2013.01); *A61B 2017/00477* (2013.01)

(58) Field of Classification Search
CPC ............ A61B 17/7001; A61B 17/7079; A61B 2017/0042; A61B 2017/00407; A61B 2017/00477; A61B 17/7074–7091
See application file for complete search history.

(56) References Cited

U.S. PATENT DOCUMENTS

| | | | |
|---|---|---|---|
| 4,271,836 A | 6/1981 | Bacal et al. | |
| 4,422,451 A | 12/1983 | Kalamchi | |
| 5,020,519 A | 6/1991 | Hayes et al. | |
| 5,297,538 A * | 3/1994 | Daniel | A61B 17/0206 600/206 |
| 5,704,937 A | 1/1998 | Martin | |
| 5,966,827 A | 10/1999 | Horvath et al. | |
| 6,551,316 B1 * | 4/2003 | Rinner | A61B 17/8866 606/205 |
| 6,716,218 B2 * | 4/2004 | Holmes | A61B 17/7079 606/105 |
| 6,739,068 B1 | 5/2004 | Rinner | |
| D566,271 S | 4/2008 | Gao et al. | |
| 7,454,939 B2 | 11/2008 | Garner et al. | |
| 8,157,809 B2 | 4/2012 | Butters et al. | |
| 8,951,258 B2 | 2/2015 | Peultier et al. | |
| 9,107,719 B2 * | 8/2015 | Gauthier | A61B 17/885 |
| 2003/0205075 A1 | 11/2003 | Strippgen et al. | |

(Continued)

*Primary Examiner* — Nicholas J Plionis
(74) *Attorney, Agent, or Firm* — Sorell, Lenna & Schmidt, LLP

(57) ABSTRACT

A surgical instrument includes a first arm having a slot and a part defining a cavity configured for disposal of a spinal implant. The part is sagittally movable relative to vertebrae and selectively fixable relative to the first arm. A second arm includes a slot and a part defining a cavity configured for disposal of the spinal implant. The part of the second arm is sagittally movable relative to the vertebrae and selectively fixable relative to the second arm. The first arm has a member that is movable within the slot of the second arm and the second arm has a member that is movable within the slot of the first arm to facilitate movement of a first vertebral surface relative to a second vertebral surface. Systems, spinal constructs, implants and methods are disclosed.

19 Claims, 7 Drawing Sheets

(56) References Cited

U.S. PATENT DOCUMENTS

| | | | |
|---|---|---|---|
| 2004/0024411 A1* | 2/2004 | Newton | A61B 17/025 606/105 |
| 2004/0176775 A1 | 9/2004 | Burkes et al. | |
| 2005/0021040 A1 | 1/2005 | Bertagnoli | |
| 2006/0111712 A1 | 5/2006 | Jackson | |
| 2006/0166534 A1* | 7/2006 | Brumfield | B25B 7/02 439/179 |
| 2007/0233143 A1 | 10/2007 | Josse et al. | |
| 2008/0119862 A1 | 5/2008 | Wicker et al. | |
| 2009/0005784 A1 | 1/2009 | Blain et al. | |
| 2009/0105547 A1* | 4/2009 | Vayser | A61B 17/0206 600/228 |
| 2009/0228051 A1 | 9/2009 | Kolb et al. | |
| 2009/0259262 A1* | 10/2009 | Nayet | A61B 17/7079 606/86 A |
| 2009/0281582 A1 | 11/2009 | Villa et al. | |
| 2010/0262198 A1 | 10/2010 | Braunschweiler et al. | |
| 2012/0078308 A1* | 3/2012 | Dziedzic | A61B 17/7086 606/264 |
| 2013/0190822 A1* | 7/2013 | Rezach | A61B 17/7085 606/264 |
| 2014/0031828 A1* | 1/2014 | Patel | A61B 17/0206 606/90 |
| 2014/0257312 A1* | 9/2014 | Solitario, Jr. | A61B 17/7079 606/90 |
| 2016/0095634 A1 | 4/2016 | Meyer | |
| 2018/0338783 A1* | 11/2018 | Mire | A61B 17/7001 |

\* cited by examiner

SURGICAL INSTRUMENT AND METHOD

TECHNICAL FIELD

The present disclosure generally relates to medical devices for the treatment of musculoskeletal disorders, and more particularly to a surgical instrument employed with a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including vertebral rods and bone fasteners for stabilization of a treated section of a spine. Rods redirect stresses away from a damaged or defective region while healing takes place to restore proper alignment and generally support vertebral members. In some cases, the spinal implants may be manipulated with surgical instruments for compression and distraction of vertebrae. This disclosure describes an improvement over these prior technologies.

SUMMARY

In one embodiment, a surgical instrument is provided. The surgical instrument includes a first arm having a slot and a part defining a cavity configured for disposal of a spinal implant. The part is sagittally movable relative to vertebrae and selectively fixable relative to the first arm. A second arm includes a slot and a part defining a cavity configured for disposal of the spinal implant. The part of the second arm is sagittally movable relative to the vertebrae and selectively fixable relative to the second arm. The first arm has a member that is movable within the slot of the second arm and the second arm has a member that is movable within the slot of the first arm to facilitate movement of a first vertebral surface relative to a second vertebral surface. In some embodiments, systems, spinal constructs, implants and methods are disclosed.

In one embodiment, the surgical instrument includes a first arm having a sagittally movable capture element. The capture element defines an opening configured for disposal of a spinal rod and includes a surface engageable with a first bone fastener connected to the spinal rod and a first vertebral surface. A second arm includes a sagittally movable capture element. The capture element of the second arm defines an opening configured for disposal of the spinal rod and includes a surface engageable with a second bone fastener connected to the spinal rod and a second vertebral surface. A linkage connects the arms to facilitate movement of the first vertebral surface relative to the second vertebral surface.

In one embodiment, a spinal implant system is provided. The spinal implant system includes a spinal rod and a surgical instrument having a pair of arms connected via a linkage. Each arm includes a sagittally movable capture element defining an opening configured for disposal of the spinal rod and including an engagement surface. A first bone fastener includes a receiver configured for disposal of the spinal rod and a shaft engageable with a first vertebral surface. A second bone fastener includes a receiver configured for disposal of the spinal rod and a shaft engageable with a second vertebral surface.

BRIEF DESCRIPTION OF THE DRAWINGS

The present disclosure will become more readily apparent from the specific description accompanied by the following drawings, in which.

DETAILED DESCRIPTION

Figure 1:
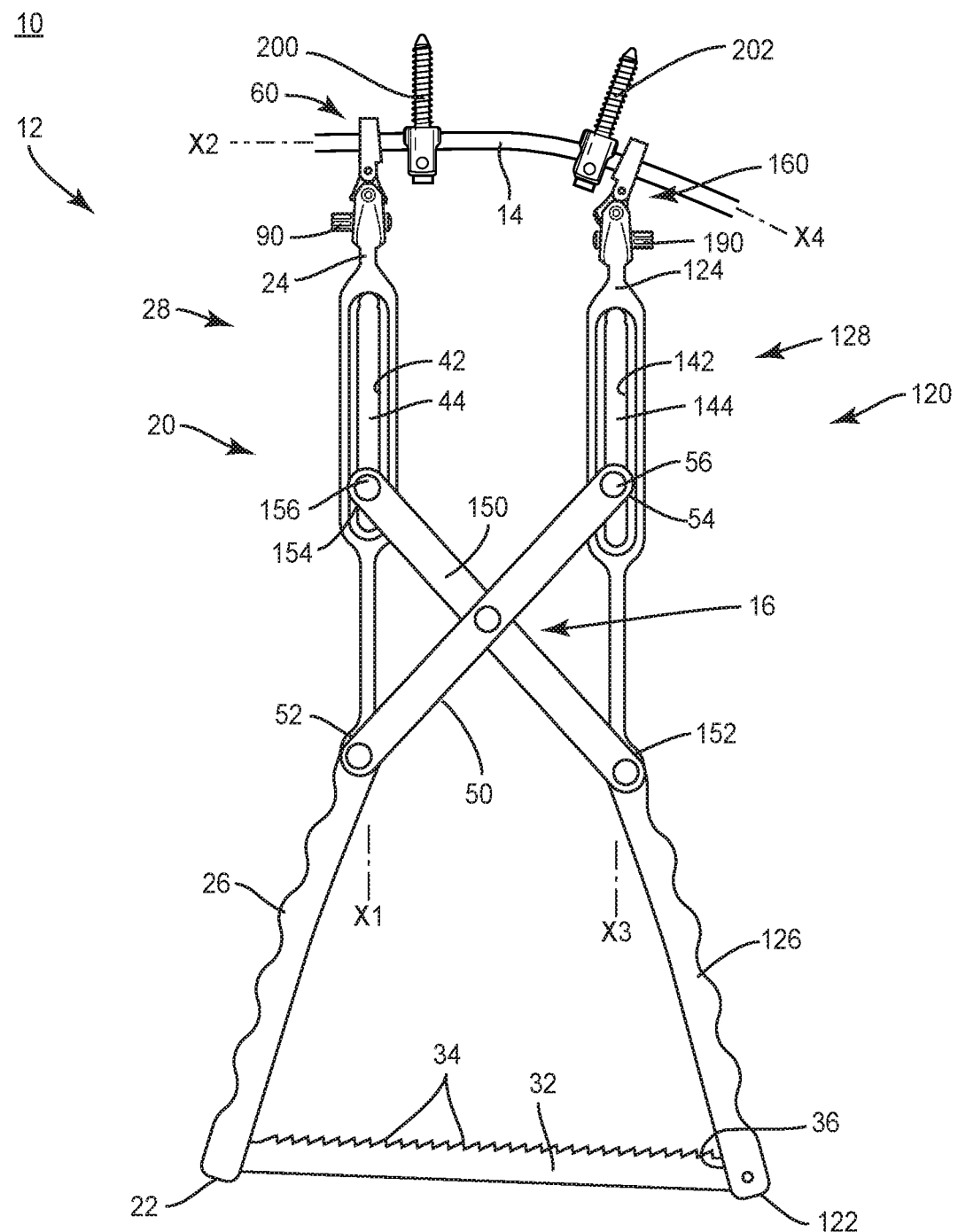
FIG. 1 is a plan view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a surgical instrument employed with a spinal implant system and a method for treating a spine. In some embodiments, the spinal implant system is configured for employment with pedicle subtraction osteotomy (PSO) and/or vertebral column resection (VCR) procedures, as described herein.

In some embodiments, the present spinal implant system includes a surgical instrument engageable with spinal implants, for example, vertebral rods and bone fasteners, connected with vertebral tissue for manipulation of the spinal implants and tissue, for example, to compress vertebrae in connection with surgical treatment, as described herein. In some embodiments, the surgical instrument is configured as a sagittal alignment compressor to manipulate vertebral tissue for compression in sagittal alignment with vertebrae. In some embodiments, the surgical instrument is configured for adjusting vertebrae in a sagittal plane. In some embodiments, the surgical instrument is configured for adjusting vertebrae in a sagittal plane to compensate for bone screws in a lordotic plane or a kyphotic plane.

In some embodiments, the present spinal implant system includes a surgical instrument engageable with spinal implants and configured with an expanded width and/or compression width. In some embodiments, the surgical instrument includes an expanded width of 70 mm and a compression width of 25 mm. In some embodiments, the surgical instrument includes one or more sliding compression slots. In some embodiments, the slots have an extended length to facilitate movement of a linkage of the surgical instrument. In some embodiments, the surgical instrument includes an adjustment knob that is configured to provide adjustment of a capture element in a sagittal plane and/or fixes the capture element at a desired angle relative to the surgical instrument and/or vertebrae.

In some embodiments, the surgical instrument is configured to provide compression of different fixation points in a lumbar or a thoracic spine. In some embodiments, the surgical instrument is configured to provide compression of two fixation points with multi-axial screws disposed in different linear planes and/or an osteotomy. In some embodiments, the surgical instrument is configured to facilitate PSO closures, VCR closures and compressions, and/or compression during transforaminal lumbar interbody fusion (TLIF) procedures.

In some embodiments, the present spinal implant system includes a surgical instrument engageable with spinal implants and configured to increase a range of compression of vertebral tissue. In some embodiments, the surgical instrument includes an engagement surface for connection and/or surface contact with spinal implants, for example, bone fasteners connected with vertebral tissue. In some embodiments, the engagement surface includes one or more mating and/or fixation elements, for example, one or more teeth, engageable with spinal implants. In some embodiments, the engagement surface is adjustable in the sagittal plane to facilitate proper compression when connecting with multi-axial screws.

In some embodiments, the present spinal implant system includes a surgical instrument engageable with spinal implants and configured to facilitate compression of the lumbar spine and/or the thoracic spine. In some embodiments, the surgical instrument is configured to adjust patient anatomy having extreme lordotic curvatures after osteotomies. In some embodiments, the surgical instrument is configured for use with the thoracic spine to provide adjustability to an inward sagittal plane for thoracic alignment.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO₄ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a surgical instrument 12. Surgical instrument 12 is configured for connection with a spinal implant, for example, a spinal rod 14. Surgical instrument 12 includes an arm 20 and an arm 120, as shown in FIG. 1. Arms 20, 120 are connected by a linkage 16 configured to facilitate relative movement of arms 20, 120. In some embodiments, surgical instrument 12 is configured as a sagittal alignment compressor to manipulate and compress a first vertebral surface relative to a second vertebral surface in a sagittal plane for sagittal alignment of vertebrae, as described. In some embodiments, surgical instrument 12 is configured for employment with PSO and/or VCR procedures, as described herein. In some embodiments, surgical instrument 12 is configured for adjusting vertebrae in a sagittal plane of a body. In some embodiments, surgical instrument 12 is configured for adjusting vertebrae in a sagittal plane to compensate for bone screws in a lordotic plane or a kyphotic plane.

Arm 20 extends between a proximal end 22 and a distal end 24. In some embodiments, a cross section and/or overall configuration of arm 20 may be variously configured, such as, for example, round, oval, oblong, square, rectangular, polygonal, irregular, uniform, non-uniform, offset, staggered, tapered, consistent or variable. In some embodiments, arm 20 may include an outer gripping surface, for example, undulating finger grips, as shown in FIG. 1, configured for gripping by a hand of a practitioner. In some embodiments, the gripping surface may include various surface configurations, for example, rough, arcuate, mesh, dimpled and/or textured. Arm 20 includes a handle 26 and an extension 28, as described herein.

Figure 2A:
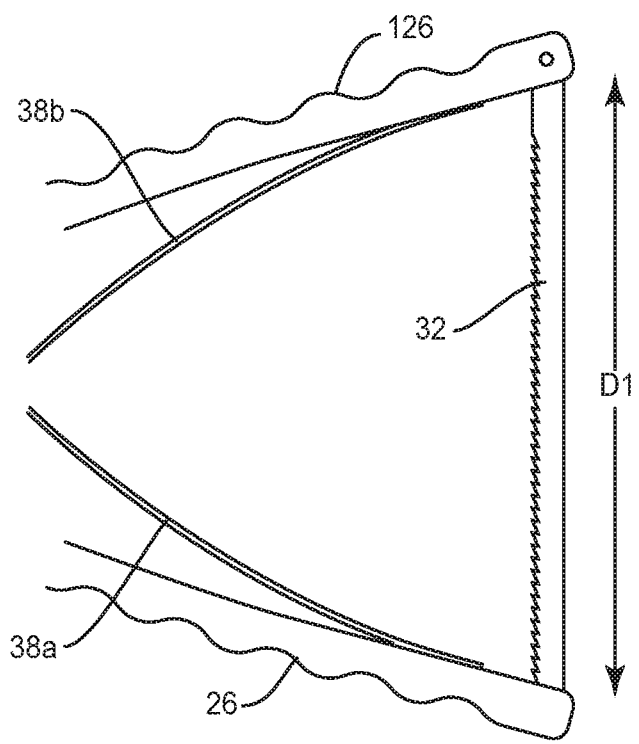
FIG. 2A is a break away view of components of one embodiment of a spinal implant system in accordance with the principles of the present disclosure.
Figure 2B:
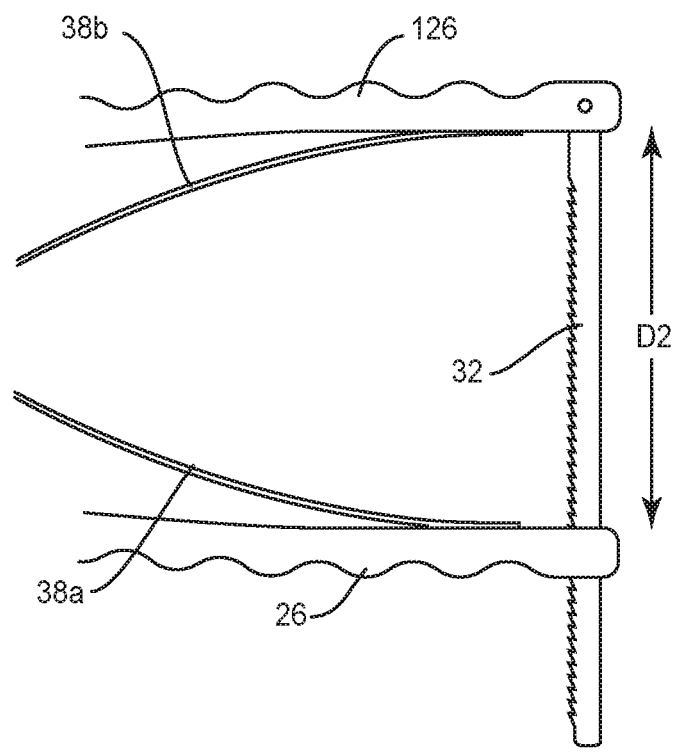
FIG. 2B is a plan view of the components shown in FIG. 2A.

Handle 26 extends at an angle relative to extension 28. Handle 26 is disposed in a plier configuration with a handle 126. Handle 26 includes a ratchet 32 having a plurality of teeth 34 engageable with a surface 36 of handle 126 to releasably fix a relative position of arms 20, 120. In some embodiments, as shown in FIGS. 2A and 2B, handle 26 includes a spring arm 38a engageable with a spring arm 38b, which causes handle 26 to be resiliently biased to an open configuration. In some embodiments, handle 26 is freely movable without bias. In some embodiments, handle 26 is non-lockable and freely adjustable such that selective orientation of arm 20 relative to arm 120 is freely adjustable.

Figure 3:
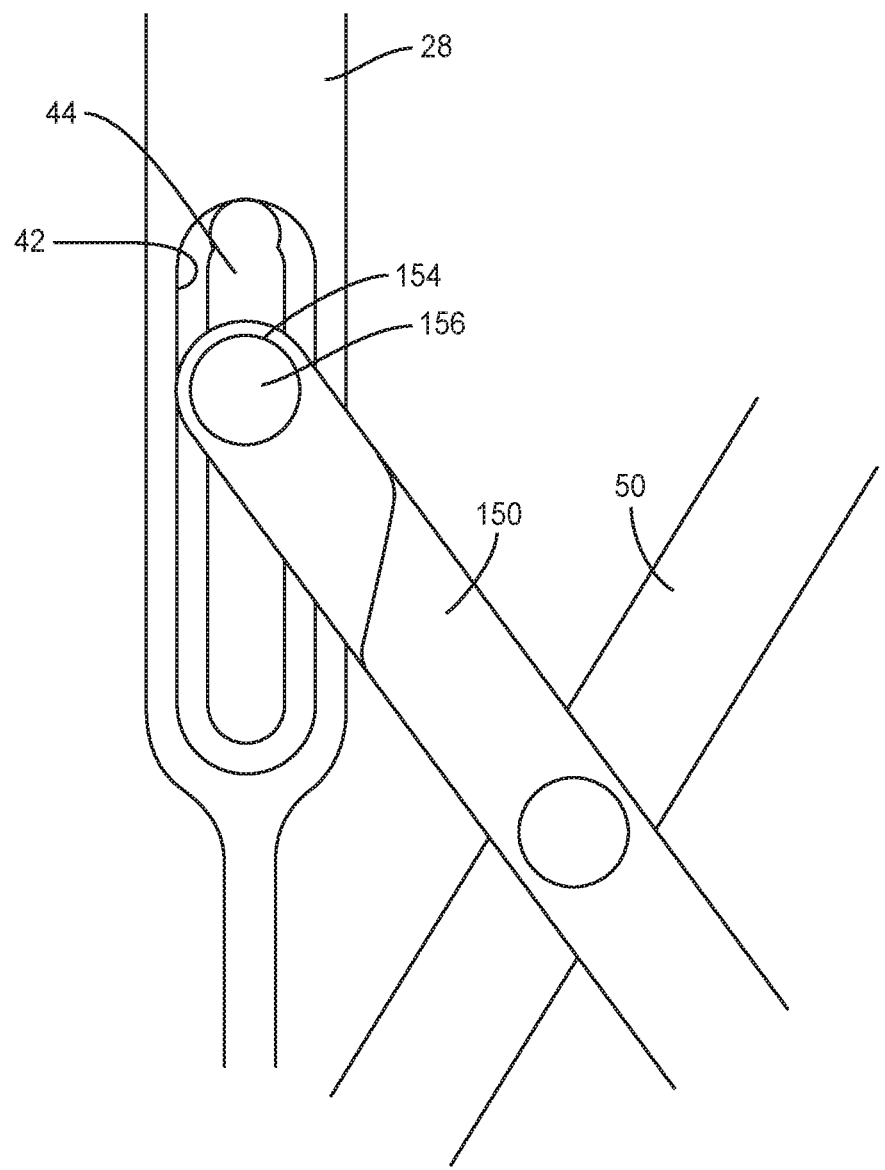
FIG. 3 is a break away view of the components shown in FIG. 1.
Figure 4:
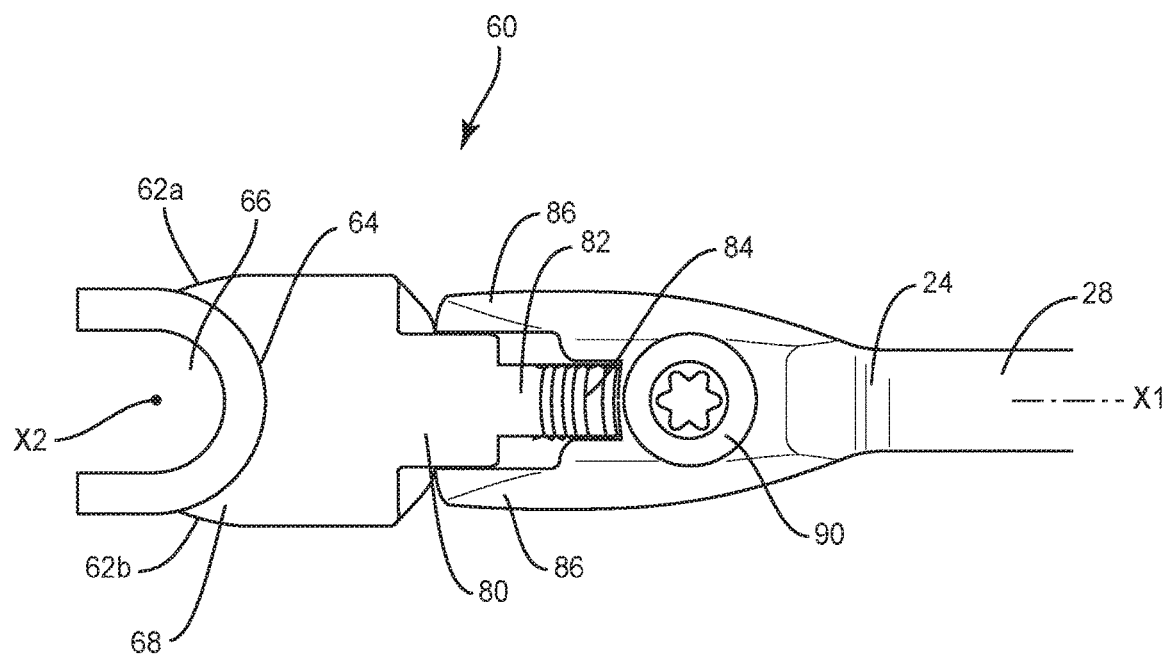
FIG. 4 is a break away plan view of components of one embodiment of a spinal implant system in accordance with the principles of the present disclosure.

Extension 28 defines an axis X1. Extension 28 includes a surface 42 that defines an elongated slot 44, as shown in FIG. 3. Slot 44 extends coaxially along extension 28. In some embodiments, slot 44 may be disposed in alternate orientations relative to extension 28, for example, transverse, perpendicular and/or other angular orientations such as acute or obtuse, coaxial and/or may be offset or staggered. Slot 44 is configured for disposal of a pivot 156 of a member, for example, a link 150 of linkage 16, as described herein.

Arm 20 includes a member, for example, a link 50 of linkage 16. Link 50 extends between an end 52 and an end 54. End 52 is pivotably connected with handle 26 to facilitate translation of link 50 and relative rotation of arms 20, 120 for compression of tissue, as described herein. Link 50 is pivotally connected to link 150 of arm 120. End 54 includes a pivot 56 configured for disposal in an elongated slot 144, as described herein. Disposal of pivot 56 with slot 144 is configured to facilitate translation of link 50 along arm 120 and relative rotation of arms 20, 120 for compression of tissue, as described herein.

Extension 28 includes a part, for example, a sagittally moveable capture element 60. Capture element 60 extends from end 24 of arm 20. Capture element 60 includes a body 62 having spaced apart extensions 62a, 62b. In some embodiments, the extensions may be disposed in alternate orientations relative to axis X1, for example, parallel, transverse and/or other angular orientations such as acute or obtuse, co-axial and/or may be offset or staggered. In some embodiments, the extensions may include hooks, legs and/or prongs comprising a fork configuration. In some embodiments, the extensions may include one or more inward projections disposed to engage a spinal implant. In some embodiments, the extensions may include one or more inward gripping surfaces, which may include surface configurations to enhance engagement with a spinal implant, for example, rough, arcuate, undulating, mesh, porous, semi-porous, dimpled and/or textured.

Body 62 and extensions 62*a*, 62*b* include an inner surface 64 that defines an open cavity, for example, a U-shaped opening 66 configured for disposal of spinal rod 14. Opening 66 extends along an axis X2 oriented transverse to axis X1. In some embodiments, body 62 includes a closed inner surface that defines a closed circular opening for disposal of spinal rod 14. In some embodiments, the opening may include alternate configurations, for example, round, oval, rectangular, polygonal, irregular, tapered, offset, staggered, uniform and non-uniform.

Body 62 includes an engagement surface 68 for connection and/or surface contact with a spinal construct having one or more spinal implants, for example, a receiver of bone fastener 200 and/or spinal rod 14. Engagement surface 68 includes an even and/or planar surface configuration engageable with one or more surfaces of the spinal construct. In some embodiments, engagement surface 68 includes one or more mating and/or fixation elements, for example, one or more teeth, engageable with one or more surfaces of the spinal construct. In some embodiments, engagement surface 68 may include one or more gripping surfaces, which may include surface configurations to enhance engagement with a spinal implant, for example, rough, arcuate, undulating, mesh, porous, semi-porous, dimpled and/or textured. In some embodiments, engagement surface 68 is adjustable in the sagittal plane to facilitate proper compression when connecting with bone fastener 200.

Figure 7:
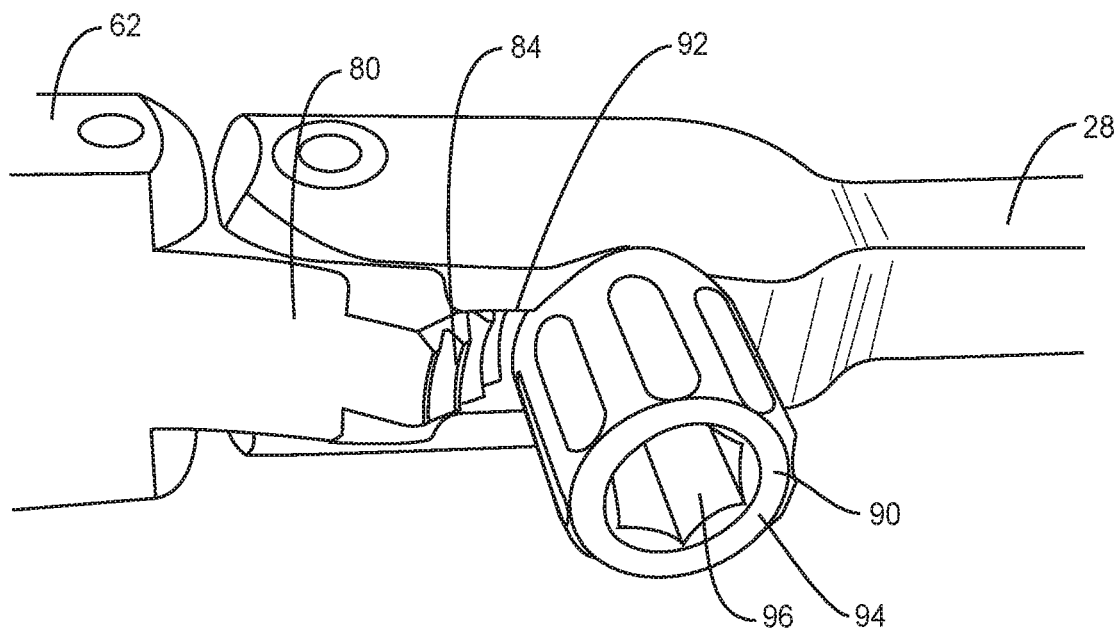
FIG. 7 is a perspective view of the components shown in FIG. 4.

Body 62 is rotatable in a sagittal plane SP of a patient body relative to extension 28 to correct a sagittal deformity, as described herein. Body 62 includes a flange 80 extending therefrom. Flange 80 includes a surface 82 that defines a gear rack 84. Extension 28 includes legs 86 pivotally connected with flange 80 to facilitate rotation of body 62 relative to extension 28 in sagittal plane SP. Extension 28 includes a screw 90 disposed transverse to axis X1. Screw 90 includes a thread form 92 and a knob 94, as shown in FIG. 7. Knob 94 includes a tool engaging portion, for example, a socket 96 configured for engagement with a surgical tool or instrument to actuate rotation of screw 90, as described herein. In some embodiments, socket 96 includes a hexagonal cross-section to facilitate engagement with a surgical tool or instrument, as described herein. In some embodiments, socket 96 may have alternative cross-sections, such as, for example, rectangular, polygonal, hexalobe, oval, or irregular.

Figure 6:
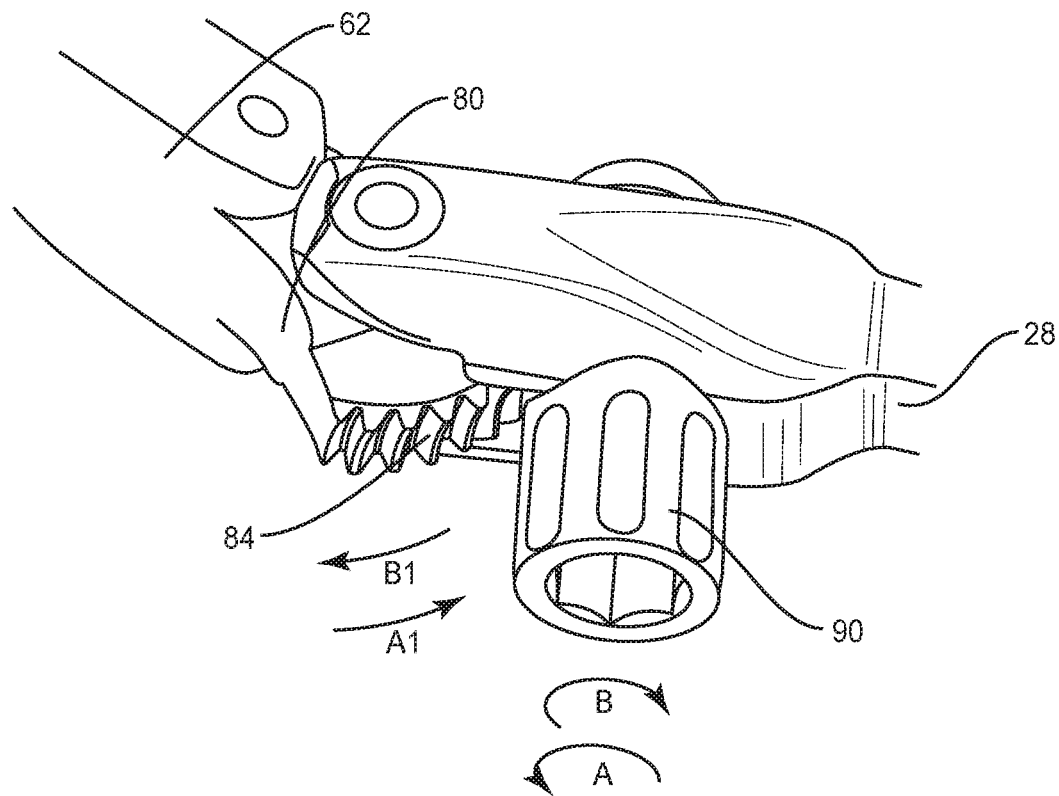
FIG. 6 is a perspective view of the components shown in FIG. 4.
Figure 8:
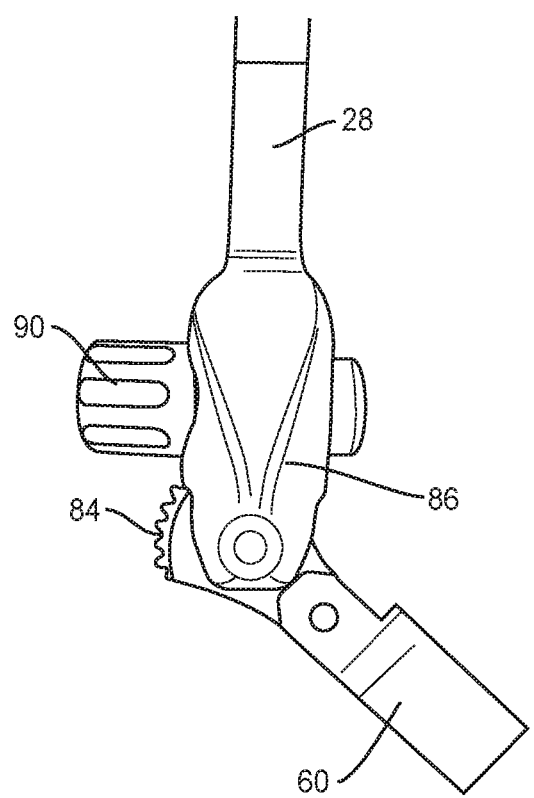
FIG. 8 is a side view of the components shown in FIG. 4.
Figure 9:
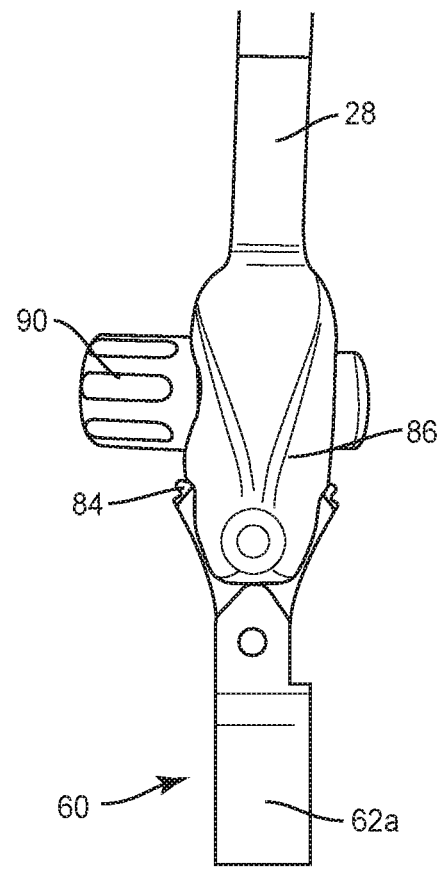
FIG. 9 is a side view of the components shown in FIG. 4.

Thread form 92 meshes with gear rack 84 to actuate rotation of capture element 60 relative to extension 28. In some embodiments, screw 90 and gear rack 84 comprise a worm gear to actuate rotation of capture element 60 relative to extension 28. For example, capture element 60 is initially fixed relative to extension 28 and disposed in a locking configuration, as described herein. To actuate rotation of capture element 60, screw 90 is rotatable, in the directions shown by arrows A and B in FIG. 6, to rotate capture element 60, as shown in FIGS. 6-8, for disposal in a selected orientation relative to extension 28 to facilitate engagement with a spinal construct having one or more spinal implants, for example a receiver of bone fastener 200 and/or vertebral tissue. For example, as screw 90 is rotated in a counter clockwise direction, as shown by arrow A in FIG. 6, thread form 92 engages gear rack 84 causing rotation of capture element 60, in the direction shown by arrow A1 in FIG. 6. As screw 90 is rotated in a clockwise direction, as shown by arrow B in FIG. 6, thread form 92 engages gear rack 84 causing rotation of capture element 60, in the direction shown by arrow B1 in FIG. 6. Capture element 60 is rotatable for adjustment, which may include incremental adjustment, for engagement with a spinal construct having one or more spinal implants relative to extension 28, as shown in FIGS. 6-8. Adjustment of capture element 60 facilitates rotation of surface 68 into selective engagement with a surface of a receiver of bone fastener 200. Surface 68 frictionally engages the surface of the receiver such that capture element 60 is fixed with bone fastener 200 and spinal rod 14 to manipulate vertebral tissue for compression in sagittal alignment with vertebrae.

Screw 90 drives gear rack 84 to rotate capture element 60 to a selected orientation relative to extension 28, for engagement with a spinal construct having one or more spinal implants, for example the receiver of bone fastener 200 and/or vertebral tissue. In some embodiments, the selected orientation includes engagement and/or fixation of surface 68 with the receiver of bone fastener 200. Upon disposal of capture element 60 and the receiver of bone fastener 200 in a selected orientation, thread form 92 is self-locking with gear rack 84 due to the friction and/or interference between the teeth of gear rack 84 and thread form 92. As such, during manipulation of surgical instrument 12 to treat vertebral tissue, as described herein, reactive and/or resistance forces generated and applied to capture element 60 are resisted and/or prevented by the engagement between gear rack 84 and thread form 92. Rotation of capture element 60 relative to extension 28 is actuated only by rotation of screw 90. The self-locking configuration and engagement of surface 68 with the receiver of bone fastener 200 creates a robust connection between components to facilitate manipulation of vertebrae and compression.

Arm 120 extends between a proximal end 122 and a distal end 124. In some embodiments, a cross section and/or overall configuration of arm 120 may be variously configured, for example, round, oval, oblong, square, rectangular, polygonal, irregular, uniform, non-uniform, offset, staggered, tapered, consistent or variable. In some embodiments, arm 120 may include an outer gripping surface, for example, undulating finger grips, as shown in FIG. 1, configured for gripping by a hand of a practitioner. In some embodiments, the gripping surface may include various surface configurations, for example, rough, arcuate, mesh, dimpled and/or textured. Arm 120 includes handle 126 and an extension 128, as described herein.

Handle 126 extends at an angle relative to extension 128. Handle 126 is disposed in a plier configuration with handle 26, as described herein. Handle 126 includes surface 36 for disposal of ratchet 32 to releasably fix a relative position of arms 20, 120. Handle 126 includes spring arm 38*b* engageable with spring arm 38*a*, which causes handle 126 to be resiliently biased to an open configuration. In some embodiments, handle 126 is freely movable without bias. In some embodiments, handle 126 is non-lockable and freely adjustable such that selective orientation of arm 20 relative to arm 120 is freely adjustable. In some embodiments, ratchet 32 allows arms 20, 120 to be adjusted between a distance D1 and a distance D2 to facilitate capture of spinal rod 14 and manipulation of vertebrae. For example, FIG. 2A shows arms 20, 120 in an expanded orientation distance D1 and FIG. 2B shows arms 20, 120 in a compressed orientation distance D2. In some embodiments, arms 20, 120 can be adjusted in a range 25 mm to 70 mm.

Extension 128 defines an axis X3. Extension 128 includes a surface 142 that defines an elongated slot 144. Slot 144 extends coaxially along extension 128. In some embodiments, slot 144 may be disposed in alternate orientations relative to extension 128, for example, transverse, perpendicular and/or other angular orientations such as acute or obtuse, coaxial and/or may be offset or staggered. Slot 144 is configured for disposal of pivot 56 of link 50, as described herein.

Arm 120 includes link 150. Link 150 extends between an end 152 and an end 154. End 152 is pivotably connected with handle 126 to facilitate rotation and/or translation of link 150 relative to arms 20, 120, as described herein. Link 150 is pivotally connected to link 50 of arm 20. End 154 includes pivot 156 configured for disposal in elongated slot 44, as described herein. Disposal of pivot 156 with slot 44 is configured to facilitate configured to facilitate translation of link 150 along arm 20 and relative rotation of arms 20, 120 for compression of tissue, as described herein.

Extension 128 includes a part, for example, a sagittally moveable capture element 160. Capture element 160 extends from end 124 of arm 120. Capture element 160 includes a body 162 having spaced apart extensions 162a, 162b. In some embodiments, the extensions may be disposed in alternate orientations relative to axis X3, for example, parallel, transverse and/or other angular orientations such as acute or obtuse, co-axial and/or may be offset or staggered. In some embodiments, the extensions may include hooks, legs and/or prongs comprising a fork configuration. In some embodiments, the extensions may include one or more inward projections disposed to engage a spinal implant. In some embodiments, the extensions may include one or more inward gripping surfaces, which may include surface configurations to enhance engagement with a spinal implant, for example, rough, arcuate, undulating, mesh, porous, semi-porous, dimpled and/or textured.

Body 162 and extensions 162a, 162b include an inner surface 164 that defines an open cavity, for example, a U-shaped opening 166 configured for disposal of spinal rod 14. Opening 166 extends along an axis X4 oriented transverse to axis X3. In some embodiments, body 162 includes a closed inner surface that defines a closed circular opening for disposal of spinal rod 14. In some embodiments, the opening may include alternate configurations, for example, round, oval, rectangular, polygonal, irregular, tapered, offset, staggered, uniform and non-uniform.

Body 162 includes an engagement surface 168 for connection and/or surface contact with a spinal construct having one or more spinal implants, for example, a receiver of bone fastener 202 and/or spinal rod 14. Engagement surface 168 includes an even and/or planar surface configuration engageable with one or more surfaces of the spinal construct. In some embodiments, engagement surface 168 includes one or more mating and/or fixation elements, for example, one or more teeth, engageable with one or more surfaces of the spinal construct. In some embodiments, engagement surface 168 may include one or more gripping surfaces, which may include surface configurations to enhance engagement with a spinal implant, for example, rough, arcuate, undulating, mesh, porous, semi-porous, dimpled and/or textured. In some embodiments, engagement surface 168 is adjustable in the sagittal plane to facilitate proper compression when connecting with bone fastener 202.

Figure 5:
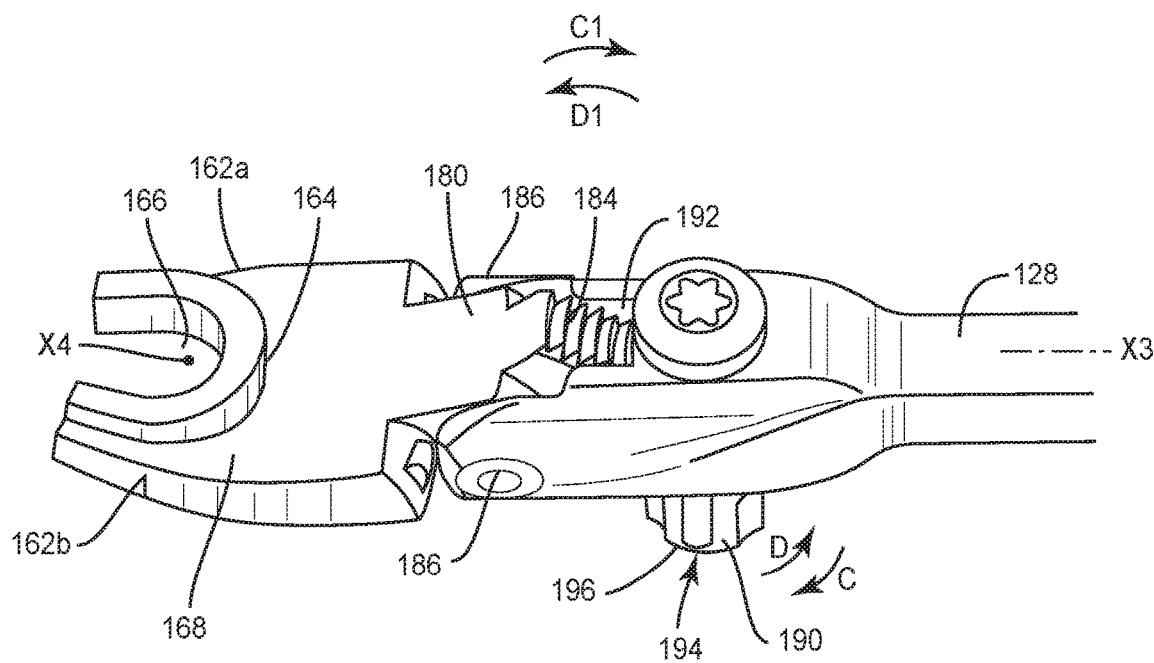
FIG. 5 is a perspective view of the components shown in FIG. 4.

Body 162 is rotatable in sagittal plane SP of a patient body relative to extension 128 to correct a sagittal deformity, as described herein. Body 162 includes a flange 180 extending therefrom. Flange 180 includes a surface 182 that defines a gear rack 184. Extension 128 includes legs 186 pivotally connected with flange 180 to facilitate rotation of body 162 relative to extension 128 in sagittal plane SP. Extension 128 includes a screw 190 disposed transverse to axis X3. Screw 190 includes a thread form 192 and a knob 194, as shown in FIG. 5. Knob 194 includes a tool engaging portion, for example, a socket 196 configured for engagement with a surgical tool or instrument to actuate rotation of screw 190, as described herein. In some embodiments, socket 196 includes a hexagonal cross-section to facilitate engagement with a surgical tool or instrument, as described herein. In some embodiments, socket 196 may have alternative cross-sections, such as, for example, rectangular, polygonal, hex-alobe, oval, or irregular.

Thread form 192 meshes with gear rack 184 to actuate rotation of capture element 160 relative to extension 128. In some embodiments, screw 190 and gear rack 184 comprise a worm gear to actuate rotation of capture element 160 relative to extension 128. For example, capture element 160 is initially fixed relative to extension 128 and disposed in a locking configuration, as described herein. To actuate rotation of capture element 160, screw 190 is rotatable, in the directions shown by arrows C and D in FIG. 5, to rotate capture element 160, as shown in FIGS. 6-8, for disposal in a selected orientation relative to extension 128 to facilitate engagement with a spinal construct having one or more spinal implants, for example a receiver of bone fastener 202 and/or vertebral tissue. For example, as screw 190 is rotated in a counter clockwise direction, as shown by arrow C in FIG. 5, thread form 192 engages gear rack 184 causing rotation of capture element 160, in the direction shown by arrow C1 in FIG. 5. As screw 190 is rotated in a clockwise direction, as shown by arrow D in FIG. 5, thread form 192 engages gear rack 184 causing rotation of capture element 160, in the direction shown by arrow D1 in FIG. 5. Capture element 160 is rotatable for adjustment, which may include incremental adjustment, for engagement with a spinal construct having one or more spinal implants relative to extension 128, as shown in FIGS. 6-8. Adjustment of capture element 160 facilitates rotation of surface 168 into selective engagement with a surface of a receiver of bone fastener 202. Surface 168 frictionally engages the surface of the receiver such that capture element 160 is fixed with bone fastener 202 and spinal rod 14 to manipulate vertebral tissue for compression in sagittal alignment with vertebrae.

Screw 190 drives gear rack 184 to rotate capture element 160 to a selected orientation relative to extension 128, for engagement with a spinal construct having one or more spinal implants, for example, the receiver of bone fastener 202 and/or vertebral tissue. In some embodiments, the selected orientation includes engagement and/or fixation of surface 168 with the receiver of bone fastener 202. Upon disposal of capture element 160 and the receiver of bone fastener 202 in a selected orientation, thread form 192 is self-locking with gear rack 184 due to the friction and/or interference between the teeth of gear rack 184 and thread form 192. As such, during manipulation of surgical instrument 12 to treat vertebral tissue, as described herein, reactive and/or resistance forces generated and applied to capture element 160 are resisted and/or prevented by the friction between gear rack 184 by thread form 190. Rotation of capture element 160 relative to extension 128 is actuated only by rotation of screw 190. The self-locking configuration and engagement of surface 168 with the receiver of bone fastener 202 creates a robust connection between components to facilitate manipulation of vertebrae and compression.

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels.

In assembly, operation and use, spinal implant system 10 including surgical instrument 12, similar to the systems and methods described herein, is employed with a surgical procedure, for example, a method for correction of deformities such as kyphosis or scoliosis, to treat a compression fracture of a vertebral body, fracture correction and/or a method for treating a patient with a PSO or a VCR. In some embodiments, one or all of the components of surgical system 10 can be delivered or utilized as a pre-assembled device or can be assembled in situ.

Figure 10:
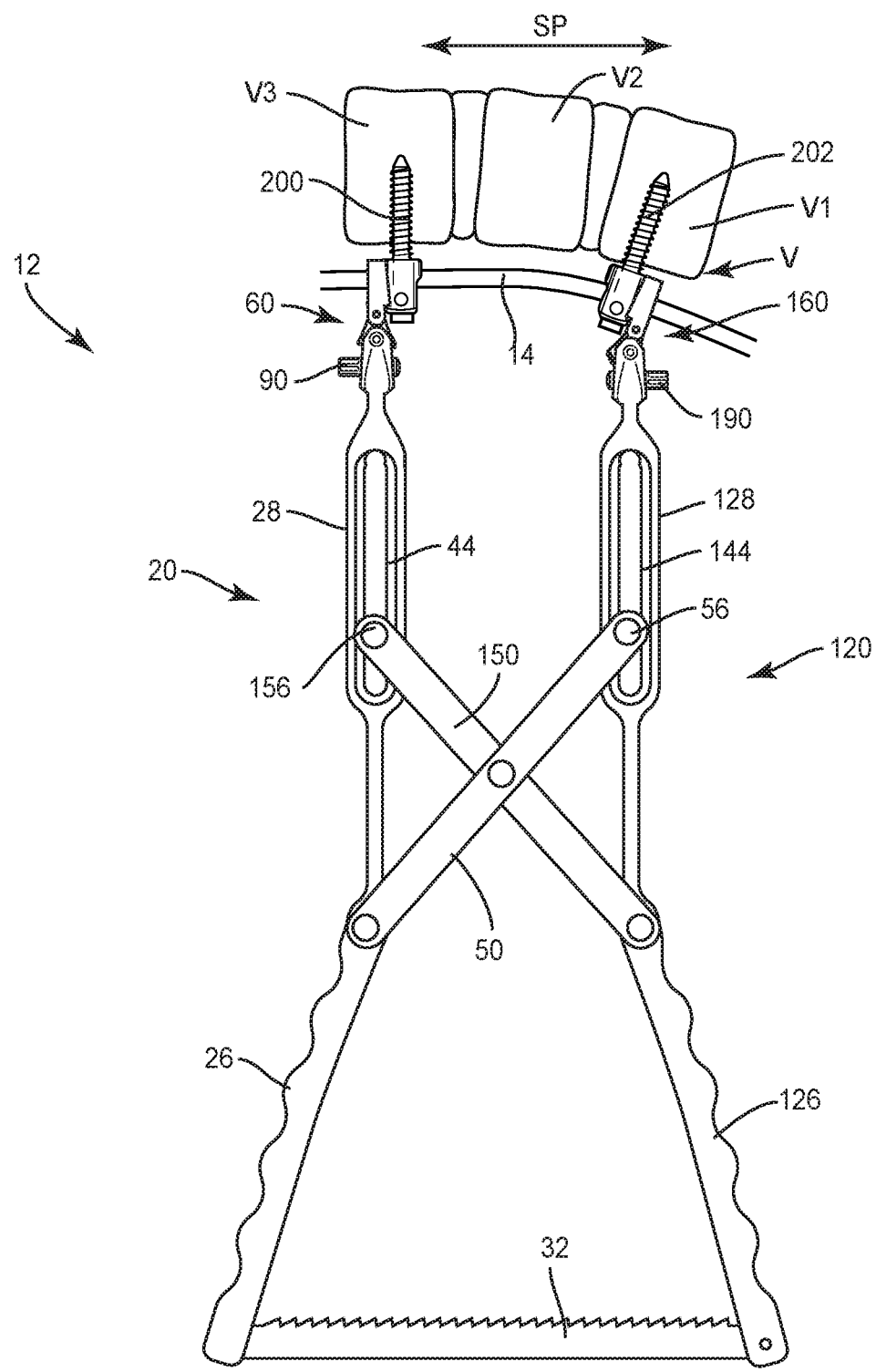
FIG. 10 is a plan view of components of one embodiment of a spinal implant system in accordance with the principles of the present disclosure disposed with vertebrae.

For example, spinal implant system 10, as shown in FIGS. 1-9, can be employed with a surgical correction treatment of a compression fracture of vertebrae V, which includes vertebral levels V1-V3, and adjacent areas within a body, as shown in FIG. 10. In operation, to treat a condition of the spine, for example, trauma of the spine, surgical instrument 12 is manipulated for engagement with spinal rod 14 for treatment of the vertebral fracture. In some embodiments, surgical instrument 12 is employed to treat vertebrae such that selected vertebra can be relatively translated for substantial axial compression or distraction to restore vertebral body height and rotated to achieve lordosis and restore curvature of the spine.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Pilot holes or the like are made in selected vertebra V1 and vertebra V3 of vertebrae V adjacent fractured vertebra V2 for receiving bone fasteners 200, 202, respectively, with fractured vertebra V2 being disposed between vertebrae V1, V3. A driver (not shown) is disposed adjacent vertebrae V at a surgical site and is manipulated to drive, torque, insert or otherwise connect bone fasteners 200, 202 adjacent vertebrae V1 and V3.

An inserter (not shown) is utilized to insert spinal rod 14 with a receiver of bone fastener 200 and a receiver of bone fastener 202. Spinal rod 14 is reduced with the receivers of bone fasteners 200, 202. A set screw (not shown) is connected with bone fastener 200 and a set screw is disposed with bone fastener 202 to provisionally secure spinal rod 14 with bone screws 200, 202.

Surgical instrument 12 is disposed adjacent the surgical site. Handles 26, 126 are disposed in an expanded orientation by spring arms 38*a*, 38*b*. Screw 90 drives gear rack 84 to rotate capture element 60, for disposal in a selected orientation relative to extension 28 to facilitate engagement with the receiver of bone fastener 200, as described herein. As screw 90 is rotated in a counter clockwise direction, as shown by arrow A in FIG. 6, thread form 92 engages gear rack 84 causing rotation of capture element 60, in the direction shown by arrow A1 in FIG. 6. As screw 90 is rotated in a clockwise direction, as shown by arrow B in FIG. 6, thread form 92 engages gear rack 84 causing rotation of capture element 60, in the direction shown by arrow B1 in FIG. 6. Capture element 60 is rotated for adjustment in sagittal plane SP relative to extension 28. Extensions 62*a*, 62*b* capture spinal rod 14 in a selected orientation such that surface 68 is selectively engaged and/or fixed, as described herein, with the surface of the receiver of bone fastener 200. Thread form 92 is self-locking with gear rack 84 due to the friction and/or interference between the teeth of gear rack 84 and thread form 92.

Screw 190 drives gear rack 184 to rotate capture element 160, for disposal in a selected orientation relative to extension 128 to facilitate engagement with the receiver of bone fastener 202. As screw 190 is rotated in a counter clockwise direction, as shown by arrow C in FIG. 5, thread form 192 engages gear rack 184 causing rotation of capture element 160, in the direction shown by arrow C1 in FIG. 5. As screw 190 is rotated in a clockwise direction, as shown by arrow D in FIG. 5, thread form 192 engages gear rack 184 causing rotation of capture element 160, in the direction shown by arrow D1 in FIG. 5. Capture element 160 is rotated for adjustment in sagittal plane SP relative to extension 128. Extensions 162*a*, 162*b* capture spinal rod 14 in a selected orientation such that surface 168 is selectively engaged and/or fixed with the surface of the receiver of bone fastener 202. Thread form 192 is self-locking with gear rack 184 due to the friction and/or interference between the teeth of gear rack 184 and thread form 192.

Handles 26, 126 are manipulated via engagement of ratchet 32 for compression to rotate vertebra V3 relative to vertebrae V1 to correct fractured vertebrae V2 along sagittal plane SP. Elements 60, 160 capture spinal rod 14 within cavities 66, 166 such that spinal rod 14 can be selectively rotated corresponding to a selected orientation of vertebrae V1-V3 for substantial axial compression to restore vertebral body height and rotated to achieve lordosis and restore curvature of the spine. During manipulation of surgical instrument 12 to treat vertebrae V, reactive and/or resistance forces generated and applied to capture elements 60, 160 are resisted and/or prevented by the friction between gear racks 84, 184 by thread forms 90, 190. The self-locking configuration and engagement of surfaces 68, 168 with the receiver of bone fasteners 200, 202 create a robust connection between components to facilitate manipulation of vertebrae and compression.

Surgical instrument 12 is temporarily fixed with vertebrae V, as described above, to temporarily stabilize and fix vertebrae V in the selected orientation to correct vertebrae V. The set screws are rotated by a driver to a locked configuration to fix the orientation of spinal rod 14 within bone screws 200, 202. In some embodiments, surgical instrument 12 is removed and a permanent rod is engaged with bone screws 200, 202.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first arm including a first body having opposite proximal and distal ends and defining an axis extending between opposite anterior and posterior surfaces, the first body defining a slot extending through the anterior and posterior surfaces, the first arm comprising a part coupled to the distal end, the part defining a cavity configured for disposal of a spinal implant, the part being rotatable relative to the first arm about the axis such that the part is sagittally movable relative to vertebrae and selectively fixable relative to the first body;
a second arm including a second body having opposite proximal and distal ends, the second body defining a slot, the second arm comprising a part coupled to the distal end of the second body, the part of the second arm defining a cavity configured for disposal of the spinal implant, the part of the second arm being sagittally movable relative to the vertebrae and selectively fixable relative to the second body,
a first member having a first end coupled to the first arm and a second end movable within the slot of the second arm; and
a second member having a first end coupled to the second arm and a second end movable within the slot of the first arm, the members being configured to move the arms to facilitate movement of a first vertebral surface relative to a second vertebral surface.

2. A surgical instrument as recited in claim 1, wherein the cavity of the first arm includes a transverse opening for disposal of a spinal rod of the spinal implant.

3. A surgical instrument as recited in claim 2, wherein the part of the first arm includes a capture element having a surface engageable with a bone fastener of the spinal implant, the bone fastener being connected to the spinal rod.

4. A surgical instrument as recited in claim 1, wherein the part of the first arm is self-locking in a selected orientation relative to the first arm.

5. A surgical instrument as recited in claim 1, wherein the part of the first arm includes a surface engageable with a first bone fastener of the spinal implant and the part of the second arm includes a surface engageable with a second bone fastener of the spinal implant, the bone fasteners being connected to one another by a spinal rod of the spinal implant.

6. A surgical instrument as recited in claim 1, wherein the instrument includes a handle having a first leg connected with the proximal end of the first body and a second leg connected with the proximal end of the second body.

7. A surgical instrument as recited in claim 6, wherein the first leg is rotatable relative to the proximal end of the first body and the second leg is rotatable relative to the proximal end of the second body.

8. A surgical instrument as recited in claim 6, wherein the first leg is spaced apart from the second leg.

9. A surgical instrument as recited in claim 6, wherein the first end of the first member is rotatably coupled to the proximal end of the first body and the first leg and the first end of the second member is rotatably coupled to the proximal end of the second body and the second leg.

10. A surgical instrument as recited in claim 1, wherein the distal end of the first body includes a transverse screw and the part of the first arm includes a gear rack engageable with the screw.

11. A surgical instrument as recited in claim 1, wherein the second end of the first member includes a pivot being movable within the slot of the second arm.

12. A surgical instrument as recited in claim 11, wherein the first end of the first member is pivotably connected with a handle.

13. A surgical instrument as recited in claim 11, wherein the second member includes a pivot being movable within the slot of the first arm.

14. A surgical instrument as recited in claim 13, wherein the first and second members are pivotably connected.

15. A surgical instrument as recited in claim 11, wherein the first end of the second member is pivotably connected with a handle.

16. A surgical instrument as recited in claim 1, further comprising a first handle coupled to the first arm and a second handle coupled to the second arm, the handles being disposed in a plier configuration and resiliently biased to an open configuration.

17. A surgical instrument as recited in claim 1, wherein the arms include a ratchet.

18. A surgical instrument comprising:
a first arm including a first body having opposite proximal and distal ends and defining an axis extending between opposite anterior and posterior surfaces, the first body defining a slot extending through the anterior and posterior surfaces, the first arm including a sagittally movable capture element coupled to the distal end, the capture element being rotatable relative to the first arm about the axis, the capture element defining an opening configured for disposal of a spinal rod and including a surface engageable with a first bone fastener connected to the spinal rod and a first vertebral surface;
a second arm including a second body having opposite proximal and distal ends, the second body defining a slot, the second arm including a sagittally movable capture element coupled to the distal end of the second body, the capture element of the second arm defining an opening configured for disposal of the spinal rod and including a surface engageable with a second bone fastener connected to the spinal rod and a second vertebral surface; and
a linkage comprising first and second members, the members connecting the arms and each having a first end coupled to one of the arms and an opposite second end disposed in one of the slots, the linkage being configured to move the arms to facilitate movement of the first vertebral surface relative to the second vertebral surface.

19. A spinal implant system comprising:
a spinal rod;
a surgical instrument including first and second arms connected via a linkage, the first arm including a first body having opposite proximal and distal ends and defining a first axis extending between opposite anterior and posterior surfaces, the first body defining a first slot extending through the anterior and posterior surfaces, the first arm including a sagittally movable capture element, the capture element being rotatable relative to the first arm about the first axis, the second arm comprising a second body including opposite proximal and distal ends and defining a second axis extending between opposite anterior and posterior surfaces, the second body defining a second slot extending through the anterior and posterior surfaces of the second body, the axes being non-coaxial, the second arm including a sagittally movable capture element, the capture element of the second arm being rotatable relative to the second arm about the second axis, the capture elements each defining an opening configured for disposal of the spinal rod and including an engagement surface;

a first bone fastener including a receiver configured for disposal of the spinal rod and a shaft engageable with a first vertebral surface; and a second bone fastener including a receiver configured for disposal of the spinal rod and a shaft engageable with a second vertebral surface, wherein the linkage is configured to move the arms to facilitate movement of the first vertebral surface relative to the second vertebral surface.

* * * * *